United States Patent [19]
Yamazaki et al.

[11] Patent Number: 5,910,423
[45] Date of Patent: Jun. 8, 1999

[54] WATER SOLUBLE POWERED FORMULATION OF REAGENT MIXTURE CONTAINING WATER-INSOLUBLE REAGENTS, AND PROCESS FOR THEIR PRODUCTION

[75] Inventors: Hiroshi Yamazaki, Nepean; Kouchi Matsumoto, Kanata, both of Canada

[73] Assignee: Ricoh Kyosan, Inc., Tokyo, Japan

[21] Appl. No.: 08/430,834

[22] Filed: Apr. 28, 1995

[51] Int. Cl.$^6$ ............................... C12Q 1/28; C12Q 1/00
[52] U.S. Cl. ................... 435/28; 435/4; 436/63
[58] Field of Search ............................ 435/28, 4; 436/63

[56] References Cited

U.S. PATENT DOCUMENTS

| | | | |
|---|---|---|---|
| 4,275,031 | 6/1981 | Fischer et al. | 435/28 |
| 4,563,143 | 1/1986 | Gerber et al. | 435/28 |
| 4,596,770 | 6/1986 | Parham et al. | 435/28 |
| 4,615,972 | 10/1986 | Gallacher | 435/28 |
| 4,828,983 | 5/1989 | McClune | 435/28 |
| 4,870,007 | 9/1989 | Smith-Lewis | 435/28 |
| 4,931,385 | 6/1990 | Block et al. | 435/28 |
| 5,006,461 | 4/1991 | Woiszwillo | 435/28 |
| 5,013,646 | 5/1991 | Woiszwillo | 435/28 |
| 5,047,318 | 9/1991 | Snyder et al. | 435/28 |
| 5,089,420 | 2/1992 | Albarella et al. | 436/63 |
| 5,176,999 | 1/1993 | McClune et al. | 435/28 |
| 5,183,742 | 2/1993 | Omoto et al. | 435/28 |
| 5,366,864 | 11/1994 | McClune et al. | 435/28 |
| 5,512,448 | 4/1996 | Yamazaki et al. | 435/28 |

FOREIGN PATENT DOCUMENTS

| | | |
|---|---|---|
| 1 218 596 | 3/1987 | Canada . |
| 1 231 633 | 1/1988 | Canada . |
| 1 246 443 | 12/1988 | Canada . |
| 1 277 895 | 12/1990 | Canada . |
| 1 281 643 | 3/1991 | Canada . |
| 1 281 644 | 3/1991 | Canada . |
| 2 028 175 | 6/1991 | Canada . |
| 1 300 499 | 5/1992 | Canada . |
| 1 303 495 | 6/1992 | Canada . |
| 1 312 277 | 1/1993 | Canada . |
| 1 321 045 | 8/1993 | Canada . |

OTHER PUBLICATIONS

Aldrich, "Catalog Handbook of Fine Chemicals," p. 1328, 1994–1995.

*Primary Examiner*—Louise N. Leary
*Attorney, Agent, or Firm*—Nixon & Vanderhye P.C.

[57] ABSTRACT

A method is provided for making a water soluble powdered formulation including a water-insoluble or difficultly-water-soluble chromogenic agent therein. The method includes first melting a water-soluble or water-miscible, heat-stable, polymeric material, e.g., PEG. The water-insoluble or difficultly-water-soluble chromogenic agent is then dissolved in such molten polymeric material. The molten polymeric material and the dissolved chromogenic agent are heated together for a predetermined period of time to provide a molten homogenate. The molten homogenate is then cooled to its solidification temperature to provide a solid homogenate. Finally, the cooled solid homogenate is pulverized to powdered form.

22 Claims, No Drawings

WATER SOLUBLE POWERED FORMULATION OF REAGENT MIXTURE CONTAINING WATER-INSOLUBLE REAGENTS, AND PROCESS FOR THEIR PRODUCTION

BACKGROUND OF THE INVENTION (i) Field of the Invention

This invention relates to a water soluble powdered formulations of reagent mixtures containing water-insoluble reagents and a process for their preparation.

(ii) Description of the Prior Art

Benzidine which has traditionally been used as a horseradish peroxidase [HRP] substrate is now known to be a carcinogen. Consequently, 3,3',5,5'-tetramethylbenzidine [hereinafter referred to as TMB] is now being used more often instead of benzidine.

Water-insoluble reagents often need to be homogenized or solubilized in aqueous solutions in chemical or enzymic analyses in order for required reaction to take place. A common strategy to achieve this condition is first to dissolve the reagents in water-miscible solvents, e.g., ethanol, p-dioxane, dimethylformamide, and dimethylsulfoxide, and then to mix the reagent solution with an aqueous medium.

The above-referred-to TMB is an example of a chromogenic substrate of HRP. A soluble TMB substrate system is used to detect HRP enzyme activity by measuring the intensity of a soluble blue or a yellow color product (after the addition of sulfuric or phosphoric acid to the blue product) as found in enzyme immunoassay [EIA]. An insoluble TMB substrate system is used to detect HRP enzyme activity by the intensity of blue colored insoluble end product found on the surface of a membrane, in membrane enzyme immunoassay, or cloth, in cloth-based enzyme immunoassay [CEIA]. These TMB systems are extremely sensitive and are the presently most commonly used reagents for detecting peroxidase labels in various EIAs. HRP is one of the most widely used enzyme labels in EIA and is at least 10-fold less expensive than alkaline phosphatase, another popular EIA enzyme. HRP catalyses the transfer of hydrogen from TMB to hydrogen peroxide ($H_2O_2$) to produce water and oxidized TMB, which becomes blue. TMB provides a highly sensitive assay of HRP as compared to other HRP substrates. Moreover, TMB is non-carcinogenic, unlike other HRP substrates, (e.g., benzidine). However, TMB is poorly soluble in water. To obtain a TMB suspension, TMB is first dissolved in water-miscible solvents, e.g., ethanol, dimethylformamide or dimethylsulfoxide before mixing. Alternatively, salts of TMB with strong acids (e.g., HCl) may be solubilized in a buffer without the aid of the solvent. However, in either case, the resulting TMB suspension is unstable, TMB being crystallized out gradually.

There are several commercial liquid formulations of TMB/HRP substrate systems in which TMB is stabilized by use of dimethylformamide, dimethylsulfoxide or proprietary surfactants or reagents. These two forms of TMB liquid formulations which are presently commercially available are "soluble" TMB reagent and "insoluble" TMB reagent. HRP action converts "soluble" TMB reagent into "soluble" blue colored products and converts "insoluble" TMB reagent into "insoluble" blue precipitate or stain. "Soluble" TMB reagent is useful for calorimetric determination of HRP as used in quantitative enzyme immunoassay based on microplates or macroporous hydrophobic cloth "segments".

A soluble TMB substrate system is used to detect HRP enzyme activity by measuring the intensity of a soluble blue or a yellow color product (after the addition of sulfuric or phosphoric acid to the blue product) found in EIA. An insoluble TMB substrate system is used to detect HRP enzyme activity by the intensity of blue colored insoluble end product found on the surface of a membrane or a cloth in membrane EIA or cloth in CEIA. These TMB systems are extremely sensitive and are the most commonly used reagents for detecting peroxidase labels in various enzyme immunoassays.

Thus, as noted above, "soluble" TMB reagent may be used for EIA for antigen on antibody-coated cloth "segment". One example of such EIA involves coating of cloth segment with an antibody, capturing of sample antigens, reaction with antibody-HRP conjugate, soluble color development with "soluble" TMB reagent, and calorimetric determination.

"Insoluble" TMB reagent is useful for visual observation of HRP action as used in qualitative EIA which visually compares the color intensity of the blue stains shown by multiple samples applied (or transferred) onto a "sheet" of cloth or membrane.

"Insoluble" TMB reagent is equally useful for dot blot assay of antigens on a sheet of membrane (e.g., nitrocellulose membrane) in the following procedure: direct spotting of sample antigens on "uncoated" membrane, blocking of the membrane with blocking proteins (e.g., non-fat dry milk), and detection of antigens by antibody-HRP as blue-stained spots. "Insoluble" TMB reagent moreover is equally useful for "Western blot" (a popular molecular biology technique) in the following procedure: fractionation of protein by gel electrophoresis, transfer of fractionated proteins to a membrane (e.g., nitrocellulose or polyvinylidene difluoride membrane), reaction with antibody-HRP conjugate, and detection of protein antigens as blue-stained bands.

TMB substrate systems can also be used to determine hemoglobin since hemoglobin, like HRP, catalyses the oxidation of TMB to colored product in the presence of $H_2O_2$. The level of plasma hemoglobin is measured by TMB reagents to monitor hemolytic conditions.

Commercially-available TMB substrate systems are all in liquid form, which adds weight and bulkiness, making packaging expensive. Furthermore, they are usually shipped via air because of their instability. Thus, packaging and shipment of the liquid formulations are not only costly to the users but also environmentally unfriendly. In addition, the TMB liquid formulations are recommended for refrigerated storage, occupying a large space in a laboratory refrigerator. Prior to use, the liquid formulations need to be equilibrated to HRP assay temperatures.

Accordingly, it is desirable to provide TMB (both "soluble" and "insoluble" TMB) in compact powder forms which are stable at ambient temperatures and which are readily and easily soluble in aqueous media. Such powder formulations not only reduce package size and shipment costs but also permit their prolonged use in fields lacking refrigeration (required for liquid formulations).

The art is replete with patents which provide for the water solubilization of water-insoluble reagents. The traditional manner of dissolving water insoluble reagents, (as noted hereinabove), has been to use non-aqueous solvents. In fact, TMB has been dissolved in the past in such non-aqueous solvents, e.g., in ethanol.

U.S. Pat. No. 4,503,143, patented Mar. 5, 1985, by B. Gerber et al, provided an enzyme immunoassay with two-part solution of TMB as a chromogen. The patentee provided an activated solution containing organic or inorganic acid salts of TMB (TMB solution), particularly an activated solution containing sulfated TMB (TMB-S). The activated solutions contained the TMB component, solvent, buffer, and hydrogen peroxide. A preferred buffer which enhanced the stability of the activated solutions was composed of citrate phosphate dissolved in water, having a pH of about 5.0. When the activated solution contained tetramethylbenzidine, the preferred solvent was methanol. However, an activated solution containing, instead, a water-soluble salt of tetramethylbenzidine, e.g., sulfated tetramethylbenzidine, had an advantage in that it avoided the need for solvents other than water.

Thus, the patentee merely provided activated aqueous or alcoholic/aqueous solutions containing TMB for immunoassay purposes.

U.S. Pat. No. 4,596,770, patented Jun. 24, 1986, by M. Parham et al, (and its corresponding Canadian Patent No. 1,246,443 patented Dec. 13, 1988), provided for the assay of peroxidase enzyme activity. The patentee taught the use of aqueous N-methylpyrrolidone as a solvent for a substrate containing tetraalkylbenzidine chromogen and a peroxide in determining peroxidase enzyme activity provides increased stability of the substrate solution and decreased substrate drift in carrying out enzyme immunoassays or enzyme-linked immunosorbent assays. By this patent it was taught provided an enzyme immunoassay or enzyme-linked immunosorbent assay in which 3,3',5,5'-tetraalkylbenzidine chromogen or an acid salt thereof and a peroxide are reacted with a peroxidase in an aqueous buffered substrate medium. The chromogen or acid salt was provided in solution in an aqueous medium containing 5 to 20% by volume of N-methylpyrrolidone (NMP).

Thus, the patentee merely provided a different solvent for an aqueous solution of TMB with low background.

U.S. Pat. No. 4,615,972, patented Oct. 7, 1986, by J. J. Gallacher, (and its corresponding Canadian Patent No. 1,231,633 patented Jan. 19, 1988), provided for the stabilization of indicators for detecting enzyme activity. The patentee provided a stabilized indicator powder for use in assays to detect the presence of peroxidase or other peroxidatively active substances. An indicator was combined with a stabilizer substance to produce a stabilized indicator powder. Preferred stabilizers were said to be solid water soluble polymers. To prepare the stabilized indicator powder, an indicator was mixed with a water-soluble polymer, e.g., polyethylene glycol, polyethyleneoxide or polyvinylpyrrolidone and derivatives thereof, followed by grinding the mixture. To prepare the stabilized indicator powder, the two compounds were first mixed with a paddle and then ground together, either with a mortar and pestle or in a ball mill for thirty minutes in the cold (i.e., at a temperature of about 4° to 8° C.). The aqueous medium into which the stabilized powdered reagent was dissolved may be either pure water or a previously prepared solution.

Thus, this patent provided a cold fusion technique for mixing the polymer with the indicator.

U.S. Pat. Nos. 5,006,461, patented Apr. 9, 1991, and 5,013,646 patented May 7, 1991, by J. E. Woiszwillo, provided a solvent system for use in increasing the solubility of TMB. The solvent system included, as a solvent, DMF, methanol, or DMSO with povidone, 1-ethyl-2-pyrrolidone polymers. The solution could be mixed directly into an aqueous buffer without precipitating the TMB being used to obtain the preferred viscosity.

Thus, this patent merely provided a new solvent system for TMB.

U.S. Pat. No. 5,024,935, patented Jun. 18, 1991, by G. J. McClune et al, (and its corresponding Canadian Patent No. 1,321,045 patented Aug. 10, 1993), provided a dye-providing composition, a diagnostic test kit, and their use in a method for ligand determination using a peroxidase labelled-receptor. The patentee taught that such a dye-providing composition comprised an aqueous solution of a water-soluble or water-dispersible polymer, e.g., a vinylpyrrolidone polymer, and an imidazole leuco dye capable of providing a dye in the presence of hydrogen peroxide and a peroxidative substance.

Thus, this patentee merely provided a stabilizer, e.g., vinylpyrrolidone, for an aqueous solution of an imidazole leuco dye.

U.S. Pat. No. 5,047,318, patented Sep. 10, 1991, by B. A. Snyder et al, provided a dye-providing composition is useful in various diagnostic assays wherein a peroxidase-labelled specific binding species is used. This composition is substantially free of peroxidase and such labelled species, and comprises an imidazole leuco dye and 4'-hydroxyacetanilide present in an amount up to about 2.5 m molar. This composition can be included as part of a diagnostic test kit.

The composition is provided in a water-soluble or water-dispersible polymer selected from the group consisting of vinylpyrrolidone polymers, acrylamide polymers, acrylic and methacrylic acid polymers, polyethylene glycols and polyamines.

Thus, the patent merely provided a solvent for the leuco dye.

U.S. Pat. No. 5,176,999, patented Jan. 5, 1993, by G. J. McClune et al, (and its corresponding published Canadian Patent Application No. 2,028,175, as well as U.S. Pat. No. 5,366,864, patented Nov. 22, 1994 by G. J. McClune), provided a buffered wash composition, insolubilizing compositions, test kits and method of use. The patented buffered aqueous composition included a dye-providing composition, a buffer and an organic solvent having a certain molecular weight and water-solubility. The wash composition also included one or more water-soluble organic solvents having a molecular weight of from about 40 to about 100. Particularly useful solvents included the lower alcohols, e.g., ethanol, n-propanol, isopropanol, n-butanol, sec-butanol, tert-butanol and others known to one skilled in the art. Other useful solvents included acetonitrile, ketones, e.g., acetone and methyl ethyl ketone, and ethers, e.g., tetrahydrofuran and 1,4-dioxane. The preferred solvents were the lower alcohols, with sec-butanol being most preferred.

Thus, this patent merely taught the use of another solvent system for an aqueous solution of a benzidine.

U.S. Pat. No. 5,238,817, patented Aug. 24th, 1993, by M. N. Bobrow et al, provided a chromogenic substrate for improving detection in a peroxidase-based assay. The patentee taught that such a substrate for detecting peroxidase activity in a peroxidase-based assay included a substantially aqueous solution of at least a 1-naphthol derivative and tetramethylbenzidine.

Thus, this patentee merely provided a stabilizer, i.e., a 1-naphthol derivative, for an aqueous solution of TMB.

Canadian Patent No. 1,218,596, patented Mar. 3, 1987, by N. Kameda, provided a competitive immunofluorescence assay and test kit. In that patent, the reagents that were incubated with the sample suspected of containing antigen to form immune complexes, were (1) fluorescent-labelled antigen, (2) anti-antigen antibody, (3) antibody against the anti-antigen antibody, and (4) a non-fluorescent non-lightscattering immunoprecipitant. Compounds that were conventionally used to precipitate proteins and that had the required non-fluorogenic properties may be used. Examples of such materials included polyethylene glycol having a molecular weight in the range of about 3,000 to about 12,000, preferably about 4,000 to 10,000, and inorganic salts, e.g., ammonium sulfate. Polyethylene glycol was a preferred immunoprecipitant.

Thus, this patentee merely taught the use of polyethylene glycol as an immunoprecipitant, and not as a solvent.

Canadian Patent No. 1,277,895, patented Dec. 18, 1990, by M. J. Powell et al, provided assay reagents. The patentee taught that the peroxidase activity of a buffered aqueous solution containing a peroxidase or a peroxidase conjugate, and TMB as a chromogen could be stabilized by the use of a particular member of the family of cyclic oligosaccharides known as cyclodextrins. The patentee provided a TMB peroxidase-substrate reagent consisting of an aqueous solution comprising TMB and β-cyclodextrin in solution. The β-cyclodextrin acted to solubilize the otherwise sparingly soluble TMB.

Thus, the patentee merely taught a new carrier containing β-cyclodextrin for an aqueous solution of TMB.

Canadian Patent No. 1,281,644, patented Mar. 19, 1991, by J. N. Eikenberry, provided a water-soluble composition comprising a peroxidase-labelled ligand analog and a water-soluble binder composition composed of at least about 50 percent, by weight, of poly(vinyl alcohol).

Thus, this patentee merely taught that an aqueous solution of a peroxidase labelled ligand can be stabilized by including therein at least 50% by weight of poly(vinyl)-alcohol.

Canadian Patent No. 1,286,986, patented Jul. 30, 1991, by W. Bloch et al, provided comprising a complex of a polymeric anion and a meriquinone of a benzidine compound, e.g., TMB. The reaction medium was aqueous to permit measurement of oxidative activity. However, the medium may also contain an organic co-solvent to control the solubilities of both the benzidine or substituted benzidine reactant and the meriquinone product. Preferred co-solvents, using horseradish peroxidase as catalyst, included iso-propyl alcohol, ethyl alcohol and dimethyl sulfoxide.

Thus, this patentee merely provided a solvent to provide an aqueous solution of a complex of a polymeric anion and a meriquinone of TMB.

Canadian Patent No. 1,290,661, patented Oct. 15, 1991, by I. A. Ismail et al, provided a stable composition from the determination of peroxidatively active substances. The stable test composition was 1,4-diisopropylbenzene dihydroperoxide and a benzidine indicator. The composition preferably provided TMB as the indicator and an organic solvent, e.g., ethanol, methoxypropanol and dimethylformamide, to dissolve the TMB.

Thus, this patentee merely provided a novel solvent for a TMB solution.

SUMMARY OF THE INVENTION (i) Aims of the Invention

The present invention has for its main object the provision of a water-soluble, powdered, form of a water-insoluble, chromogenic agent.

Another object of the present invention is to provide a method for preparing such water-soluble powder.

Yet another object of this invention is a provision of a method for making an aqueous solution for carrying out an enzyme immunoassay.

(ii) Statements of Invention

The present invention provides a method for making a water-soluble, powdered formulation of a water-insoluble or difficultly-water-soluble chromogenic agent, which comprises: melting a water-soluble or water-miscible, heat-stable, polymeric material; dissolving the chromogenic agent which is difficultly-water-soluble or water-insoluble in that molten polymeric material; heating such dissolved solid chromogenic agent/molten polymeric material for a predetermined period of time to provide a molten homogenate; cooling the molten homogenate to its solidification temperature; and pulverizing such solidified homogenate to powdered form.

The present invention also provides a water soluble or dispersible powdered formulation comprising: a ground, powdered, homogenate of a solid water-insoluble or difficultly-water-soluble chromogenic agent which has been dissolved in a molten, water-soluble or water-miscible, heat-stable polymeric material, and then cooled and powdered, in admixture with a selective reagent to enable dissolution in, or admixture thereof with, water.

(iii) Other Features of the Invention

By a feature of such method, the polymeric material is polyethylene glycol (PEG), preferably of molecular weight of about 1,000 to 10,000.

By another feature of such method, the test reagent is 3,3',5,5'-tetramethylbenzidine, or is 4-chloro-1-naphthol.

In another feature of such method, the powdered TMB dissolved in molten PEG, i.e., the homogenate, is mixed with citrate buffer powder mix, a mixture of citric acid and sodium citrate powder and sodium perborate, and is dissolved in water to provide a soluble TMB test reagent.

In still another feature of such method, the powdered homogenate described above as a soluble test reagent is mixed with dextran sulfate or with cellulose sulfate and is added to water, to provide an insoluble TMB test reagent.

By yet another feature of the method, the polymer is polyethyleneglycol, the test reagent is 3,3',5,5'-tetramethylbenzidine, the buffer is ethylenediaminetetraacetate, and the perborate is sodium perborate.

By still another feature of the method, the polymer is polyethyleneglycol, the test reagent is 3,3',5,5'-tetramethylbenzidine, the buffer is a phosphate salt, and the perborate is sodium perborate.

By yet a further feature of the invention, the method includes the step of mixing the powdered homogenate mixture with dextran sulfate or with cellulose sulfate, and then dispersing such mixture in water, thereby to provide a stable, insoluble TMB test reagent.

By another feature of such method the polymer is poly-ethylene glycol, the test reagent is 4-chloro-1-naphthol, (CN), and the method includes the step of mixing the powdered homogenate mixture with sodium perborate to provide an insoluble CN test reagent.

By yet another feature of the method, the powdered homogenate/reagent mixture has a particle size of about 0.01 to about 0.5 mm.

(iv) Generalized Description of the Invention

While the water-soluble or water-miscible, heat-stable polymeric material used is PEG, other analogous polymers may be used. Other water-soluble or water-dispersible polymers which may be used include vinyl pyrrolidone polymers, acrylamide polymers, acrylic and methacrylic acid polymers, polyethylene oxides and polyamines. These polymers can be either homo- or copolymers. Representative examples of useful polymers include, but are not limited to: polyvinyl pyrrolidones, polyacrylamides, polyacrylates, polymethacrylates, polyamines, polyethylene oxides, poly(acrylic acid-co-methyl acryline) (90:10 weight ratio), poly(acrylamide-co-acrylic acid) (50:50 weight ratio), polyamines and vinyl pyrrolidone polymers, that is a homo- or co-polymer prepared from vinylpyrrolidone, poly(vinylpyrrolidone), poly(vinylpyrrolidone-co-acrylic acid) and poly(vinylpyrrolidone-co-acrylamide). Among such alternatives are: neutral surfactants which are solid but which can be melted at temperatures below about 120° C., and which are mild to enzymes, e.g., Bri; 58, 72 and 78.

The PEG preferably used has the following properties: <M.W. 600 liquid, while >M.W. 600 solid. The preferred PEG has a M.W. of about 3,350, though PEG having M.W. of about 1,000 to about 10,000 can be used. While it is not desired to be restricted to any particular theory, it is believed that PEG interacts with aromatic hydrocarbons via its ethylene residues. Its ether oxygen atoms strongly interact with water, forming hydrogen bonds with the H atom of water. Thus, PEG and its hydrocarbon complexes are soluble in water.

The temperature of heating, and time to dissolve the test reagent on the molten polymer vary from about 40° C. to about 120° C. and from about 30 to about 120 minutes, depending on the polymeric material and the amount thereof used.

While the preferred test reagent used is TMB, other analogous substitutes for HRP may be used. For example, 4-chloro-1-naphthol(CN) is commonly used as an insoluble HRP assay system, but it needs to be dissolved in organic solvents (e.g., ethanol) before it becomes miscible in an aqueous solution. Accordingly, CN can be dissolved according to the broad teachings of the present invention. Consequently, the present invention is applicable to reagents for other enzymes whose substrate system requires the use of a water-insoluble substrate.

The solidified homogenate of the polymeric material and the water-insoluble test reagent is ground to a powder. A suitable powder size is from about 0.01 to about 0.5 mm.

While the TMB/PEG powder may be mixed with citric acid buffer powder and then mixed with sodium perborate to provide stable and soluble test reagents, it is possible to provide soluble test reagents by using other buffers, e.g., ethylenediaminetetraacetate (EDTA), or a phosphate as buffers by adding the buffer to the above-described soluble TMB reagent.

While the TMB/PEG powder is formulated with dextran sulfate (preferably prepared from dextran of MW about 5,000) to provide insoluble test reagents by adding it to the above-described soluble TMB reagent, it is possible to provide insoluble test reagents by using other agents, e.g., sodium cellulose sulfate. If the test reagent contains CN in place of TMB, CN/PEG powder may be mixed with sodium perborate without any buffer system to provide an insoluble test reagent, as an HRP substrate system.

DESCRIPTION OF PREFERRED EMBODIMENTS

The invention is described by way of the following examples.

EXAMPLE 1

Preparation of TMB Powder

One procedure is as follows:

(A) Place 1 kg of PEG, MW about 3,350 (but which can have MW 1,000 to 10,000) in a stainless container having a cover (e.g., a cap).

(B) Melt PEG by heating it in the stainless steel container at 80° C. without the cover for about 1 hour until all air bubbles are expelled and become clear. (The temperature can be from about 40 to about 120° C. depending on the MW of the PEG).

(C) Add about 4 to about 4.5 g of TMB and dissolve the TMB completely therein by mixing.

(D) Continue heating at 80° C. for about 1 to 2 hours with the cap on.

(E) Cap the stainless steel vessel tightly and cool to room temperature.

and (F) Crush the mass to a powder by means of a pulverizer to a size of 0.01 to 0.5 mm.

The following are typical TMB substrate reagents.

EXAMPLE 2

Soluble TMB Substrate Reagent in Powder Form

| | |
|---|---|
| TMB/PEG powder (prepared as above) | 50 g |
| citric acid buffer powder mix (citric acid and sodium citrate mixture, to provide a pH of 4 to 6) | 7.608 g |
| sodium perborate monohydrate | 0.392 g |

Usage: Dissolve 3 g of soluble TMB substrate reagent in 100 ml water.

EXAMPLE 3

Insoluble TMB Substrate Reagent in Powder Form

Add 2 g of dextran sulfate to above soluble TMB substrate reagent. Usage: Dissolve 3 g of the insoluble TMB substrate reagent in 100 ml water.

EXAMPLE 4

Use of PEG in CN HRP—Substrate System 4-chloro-1-naphthol (CN) is another peroxidase substrate for immunoblotting, producing an insoluble dark blue to purple color. As CN itself is not soluble in an aqueous medium, commercially available assay reagents are dissolved in an organic solvent. Using the same principle as used for TMB, PEG can be utilized as a carrier for CN to solubilize it in aqueous media.

The following is a typical example of such preparation. One gram (or 1 kg) of PEG, having a MW of about 3,350 was melted and heated at 80° C. until the molten product becomes very clear. Then 7 mg (or 7g) of powdered CN was completely dissolved into it. The homogenate was cooled to room temperature. The solidified homogenate was crushed and powdered.

For use of such powdered homogenate on an assay, 1 g of the above product was mixed with 2.5 mg of sodium perborate monohydrate. This mixture can be used without adjusting the pH or the addition of a citrate buffer. Thirty-five mg of powder reagent dissolved in one ml water was used as working solution.

CONCLUSIONS

The following are some advantages of the powder reagent system of this invention.

(1) Powdered form preparations provide lower weight and bulkiness. Therefore they can be shipped in small-sized packages, occupy less storage space and require less delivery cost. The use of less package material is more environmentally friendly.

(2) The powdered form can be stored at room temperature for at least one year if kept away from moisture and light. If it is refrigerated, it should be stable for many years.

(3) The powder is easily and quickly dissolved in water and no filtration is necessary. Such solution is stable at least for one day.

(4) TMB, the carrier PEG and all other of component chemicals used are quite safe in nature and are easy to handle.

(5) This preparation is usable for not only CEIA but also for all other EIA and ELISA applications which use peroxidase with low background.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A method for preparing a water-soluble powdered formulation of test reagent containing a solid chromogenic agent which comprises:

(1) melting a water soluble heat-stable polymeric material to provide a molten polymeric material;

(2) dissolving said solid chromogenic agent in said molten polymeric material;

(3) heating said dissolved solid chromogenic agent/ molten polymeric material for a predetermined period of time to provide a molten homogenate;

(4) cooling said molten homogenate to its solidification temperature to provide a solidified homogenate; and (5) pulverizing said solidified homogenate, to provide powdered homogenate reagent.

2. The method of claim 1 wherein said water soluble heat-stable polymeric material is polyethylene glycol.

3. The method of claim 2 wherein said polyethylene glycol has a molecular weight of about 1000 to about 10,000.

4. The method of claim 1 wherein said polymeric material is selected from the group consisting of polyvinyl pyrrolidones, polyacrylamides, polyacrylates, polymethacrylates, polyamines, polyethylene oxides, poly (acrylic acid-co-methyl acryline) (90:10 weight ratio), poly (acrylamide-co-acrylic acid) (50:50 weight ratio), polyamines and vinyl pyrrolidone polymers, that is a homo- or co-polymer prepared from vinylpyrrolidone, poly (vinylpyrrolidone), poly-(vinylpyrrolidone-co-acrylic acid) and poly(vinylpyrrolidone-co-acrylamide).

5. The method of claim 2 wherein said test reagent is 3,3',5,5'-tetramethylbenzidine.

6. The method of claim 3 wherein said test reagent is 3,3',5,5'-tetramethylbenzidine.

7. The method of claim 2 wherein said test reagent is 4-chloro-1-naphthol.

8. The method of claim 1 including the step of mixing said powdered homogenate with a buffer to provide a buffered homogenate powder; and then further mixing said buffered homogenate powder with a perborate, thereby to provide a stable, water-soluble test reagent.

9. The method of claim 8 wherein said water soluble heat stable polymeric material is polyethyleneglycol; wherein said test reagent is 3,3',5,5'-tetramethylbenzidine; wherein said buffer is a mixture of citric acid and sodium citrate powder; and wherein said perborate is sodium perborate.

10. The method of claim 8 wherein said heat stable polymeric material is polyethyleneglycol; wherein said test reagent is 3,3',5,5'-tetramethylbenzidine; wherein said buffer is ethylenediaminetetraacetate; and wherein said perborate is sodium perborate.

11. The method of claim 8 including the step of mixing said powdered homogenate with dextran sulfate or with cellulose sulfate, to provide an intermediate mixture; and dispersing said intermediate mixture in water, thereby to provide a stable, insoluble test reagent.

12. The method of claim 11 wherein said heat stable polymeric material is polyethylene glycol; and wherein said test reagent is 3,3',5,5'-tetramethylbenzidine; thereby to provide a stable, insoluble TMB test reagent.

13. The method of claim 8 wherein said heat stable polymeric material is polyethylene glycol; wherein said test reagent is 4-chloro-1-naphthol; and including the step of mixing said powdered homogenate with sodium perborate to provide a stable, insoluble CN test reagent.

14. The method of claim 2 wherein said powdered homogenate/reagent mixture has a particle size of about 0.01 to about 0.5 mm.

15. A powdered, water-soluble powdered formulation comprising: a ground, powdered, homogenate of a chromogenic agent, which has been dissolved in a molten, water-soluble heat-stable polymeric material and subsequently cooled to provide a solid homogenate which is ground to a powder, in admixture with a selective reagent to enable dissolution in water.

16. The formulation of claim 15 wherein said chromogenic agent is 3,3',5,5'-tetramethylbenzidine and wherein said heat stable material is polyethylene glycol.

17. The formulation of claim 16, wherein said polyethylene glycol has a molecular weight of about 1000 to about 10,000.

18. The formulation of claim 15 wherein said chromogenic agent is 4-chloro-1-naphthol and wherein said polymer is polyethylene glycol.

19. The formulation of claim 18, wherein said polyethylene glycol has a molecular weight of about 1000 to about 10,000.

20. The method of claim 1 wherein said solid chromogenic agent is water-insoluble.

21. The method of claim 20 wherein said test reagent is 3,3',5,5'-tetramethylbenzidine.

22. The powdered formulation of claim 15 wherein said chromogenic agent is water-insoluble.

* * * * *